(12) United States Patent
Moos

(10) Patent No.: US 6,368,868 B1
(45) Date of Patent: Apr. 9, 2002

(54) METHOD AND APPARATUS FOR DETECTING THE OXYGEN CONTENT OF A GAS

(75) Inventor: Ralf Moos, Friedrichshafen (DE)

(73) Assignee: Dornier GmbH, Friedrichshafen (DE)

( * ) Notice: Subject to any disclaimer, the term of this patent is extended or adjusted under 35 U.S.C. 154(b) by 0 days.

(21) Appl. No.: 09/447,357

(22) Filed: Nov. 22, 1999

(30) Foreign Application Priority Data

Nov. 20, 1998 (DE) .......................................... 198 53 595

(51) Int. Cl.⁷ .............................................. G01N 27/416
(52) U.S. Cl. ............................. 436/151; 422/94; 422/98
(58) Field of Search ................................ 204/428, 426, 204/408, 424; 73/40; 205/785; 436/151; 422/94, 98

(56) References Cited

U.S. PATENT DOCUMENTS

| 5,389,218 A | * | 2/1995 | Bonne et al. | .......... 204/153.18 |
| 5,389,225 A | * | 2/1995 | Aagard et al. | ............... 204/426 |
| 6,222,166 B1 | * | 4/2001 | Lin et al. | ..................... 219/538 |

* cited by examiner

Primary Examiner—Jill Warden
Assistant Examiner—Samuel P Siefke
(74) Attorney, Agent, or Firm—Crowell & Moring LLP

(57) ABSTRACT

In a method for detecting oxygen concentration in a gas, a functional material in the form of a layer or film made of a semiconducting metal oxide, whose thermoelectric power can be represented as a function of partial oxygen pressure, is subjected to the gas to be analyzed. A temperature difference is created between two points on the functional material, and the voltage difference between the two points of the functional material that are at different temperatures is determined as a measure of oxygen concentration.

13 Claims, 3 Drawing Sheets

METHOD AND APPARATUS FOR DETECTING THE OXYGEN CONTENT OF A GAS

BACKGROUND AND SUMMARY OF THE INVENTION

This application claims the priority of German patent document 198 53 595.3, filed Nov. 20, 1998, the disclosure of which is expressly incorporated by reference herein.

The invention relates to a method and apparatus for determining the oxygen content of a gas.

Increasingly stringent auto emission standards and pressure to reduce fuel consumption of internal combustion engines are compelling automobile manufacturers to develop new concepts for internal combustion engines. It has been shown that the above two requirements can best be harmonized by operating the internal combustion engine with excess air (that is, in a so-called "lean" mode, with an air/fuel ratio $\lambda>1$). This modern "lean concept" requires that the oxygen level of the exhaust be known precisely. However, the principle of the conventional potentiometric oxygen sensor (lambda probe) can be implemented only at high cost for the high oxygen concentrations that occur in such lean exhausts.

For measuring exhaust oxygen content in the lean range, amperometric probes on the limiting current principle ("limiting current probes") have been proposed. Such probes can be made of a material that conducts oxygen ions, as disclosed for example in Kleitz M., Siebert E., Fabry P., Fouletier J.: Solid-State Electrochemical Sensors; In: Sensors. A Comprehensive Survey; Chemical and Biochemical Sensors Part I. Göpel W. et al. (pub.), VCH-Verlag, Weinheim, 1991, pages 341–428; see also German patent documents DE 44 47 033, DE 44 08 361, DE 43 91 637, and DE 27 11 880. It is also possible however to utilize the oxygen partial pressure dependence of the electrical conductivity of a metal oxide material as a sensor effect to produce a sensor whose electrical resistance R, due to the oxygen partial pressure $pO^2$ of the exhaust, gives information on the oxygen content of the exhaust. See Howarth D. S., Micheli A. L.: A Simple Titania Thick Film Exhaust Gas Oxygen Sensor, SAE 840140, 1984; Schonauer U.: Strontium Titanate Oxygen Sensors in Thick Film Technology; Dissertation, Karlsruhe 1990; Gerblinger J.: Oxygen Sensors Based on Sputtered Strontium Titanate Layers; Dissertation, Karlsruhe 1991; and Schonauer U.: Thick Film Oxygen Sensors Based on Ceramic Semiconductors. Technisches Messen 56 [6] 260–263, 1989. Doped titanium oxide ($TiO_2$) and strontium titanate ($SrTiO_3$) have been investigated in particular depth, as such titanium oxides have sufficient chemical stability to withstand the harsh operating conditions in the exhaust line of an internal combustion engine. However, the electrical resistance of sensors made from these compounds, like most other metal oxides, has a very high temperature dependence, requiring expensive heat regulation combined with comprehensive design measures to compensate for the effects of sudden temperature changes.

It has also been proposed to use cuprates (e.g. $La_2CuO_{4+d}$) because their electrical conductivity is independent of temperature precisely in the range of high oxygen level, i.e, at $\lambda>1$. See German patent documents DE 42 02 146, DE 42 44 723, DE 43 25 183 and Blase R.: Temperature-dependent Oxygen Sensors with Short Adjustment Time Based on $La_2CuO_{4+d}$ Thick Layers; Dissertation, Karlsruhe 1996. However, cuprates are unsuitable for use in the exhaust line as they are chemically somewhat unstable and decompose at high temperatures and/or low oxygen partial pressures (e.g. short-term operation with "rich" mixtures, ($\lambda<1$).

Lanthanum ferrites doped with alkaline earths have far greater chemical stability than cuprates. (See German patent document DE 44 18 054.) By comparison to $SrTiO_3$, the temperature dependence of their electrical conductivity is lower in the lean exhaust range as well ($\lambda>1$). However, sensors made from these materials have greater temperature dependence on electrical resistance than sensors based on cuprates.

European patent document EP 0 062 994 proposes partial replacement of the titanium (Ti) in $SrTiO_3$ by iron (Fe). Sensors made from the compound $SrTi_{0.7}Fe_{0.3}O_{3-d}$ in lean atmospheres above 500° C.–600° C. have far lower temperature dependence of electrical resistance, but their oxygen partial pressure dependence is according to $R \sim pO_2^{-1/5}$.

Advantageously, such resistive oxygen sensors are made by thick film technology. A heating resistor film is applied to one flat side of an electrically nonconducting substrate, and a sensitive functional layer and possibly a temperature-measuring resistor are applied to the other flat side. This sensor arrangement is disposed in a protective housing and provided with a lead.

The resistive principle has the advantage that the oxygen content of a gas can be determined by means of a simple resistance measurement. It has the disadvantage however that in resistance measurement not only the material properties in the form of the specific electrical resistance but also the geometry of the sensitive functional layer are involved. The width and length of a film can be created well and reproducibly. However, the manufacturing of a film thickness that is exactly reproducible involves expensive process technology. Another difficulty arises when such sensors are to be operated in harsh environments such as in the exhaust line of an automobile or a power plant. Because of abrasion and other mechanical effects such as chipping on a microscopic scale, the geometry of the film changes and thus the sensor characteristic alters over time.

Another major disadvantage is based on the morphology of the sensitive films. Such polycrystalline functional layers have grain boundary layers that have different electrical behaviors to the insides of the grains. This phenomenon is even used as a measuring effect, for example in gas sensors made from $SnO_2$ films. See Ruhland B., Becker T., Müller G.: Gas-kinetic Interactions of Nitrous Oxides with $SnO_2$ Surfaces. Sensors and Actuators B 50 85–94, 1998 and Mosley P. T.: Solid-State Gas Sensors. Meas. Sci. Technol. 8 223–237, 1997. In operation, a changing grain boundary layer leads to undesirable drift of the sensor characteristic and sometimes to losses of sensitivity as well.

For precise results, particularly in the lean range, four-wire technology must be used for measurement at the sensitive functional layer, as this is the only way for contact resistances between the electrode and the functional layer to be calculated. This is important because contact resistances usually change with the oxygen partial pressure of the gas atmosphere as well. For this reason, additional expensive electrical connections are necessary.

Measuring an electrical voltage, for example with a simple limiting current sensor, is even simpler than using an electrical resistance. In this case, however, the diffusion constant of the diffusion barrier, which is yet another temperature- and material-dependent parameter, is a factor in the measured signal. Moreover, such a sensor is not easy to build and is very expensive because of the expensive multilayer technology.

One object of the invention is to provide a measuring method and apparatus for determining the oxygen content of gases, that overcomes the disadvantages of the prior art referred to above.

This and other objects and advantages are achieved by the detection method and apparatus according to the invention, in which a functional material in the form of a layer or film of a semiconducting metal oxide, whose thermoelectric power can be represented as a function of partial oxygen pressure, is subjected to the gas to be analyzed. A temperature difference is generated between two points on the functional material, and the voltage difference between the two points is measured. Since such voltage difference depends on the thermoelectric power of the functional material, it reflects the oxygen concentration of the gas to be analyzed. The voltage difference is also referred to hereinafter as the output signal of the transducer.

In a preferred embodiment, the temperature difference between the two points on the functional layer that are at different temperatures is determined by suitable direct or indirect measuring methods.

Another embodiment of the invention also considers the temperature of the functional layer.

If the transducer is operated above a temperature at which the thermoelectric power of the functional layer is a function of the oxygen partial pressure of the environment, the oxygen content of the gas surrounding the sensor can be determined from the sensor output signal, possibly considering the temperature difference between the two points at different temperatures on the functional layer.

The method and apparatus according to the invention can be used in particular to:

determine the oxygen content of exhaust gases f from furnaces (power plants and domestic);

determine the oxygen content of exhaust gases from internal combustion engines such as gasoline or diesel engines;

in medicine, detect the oxygen content of air exhaled from the body.

Other objects, advantages and novel features of the present invention will become apparent from the following detailed description of the invention when considered in conjunction with the accompanying.

DETAILED DESCRIPTION OF THE DRAWINGS

The sensor according to the invention uses the thermoelectric properties of metal oxides. The thermoelectric power $\eta$ (also called Seebeck coefficient in the literature) of oxidic semiconductors theoretically has the curve shown in FIG. 1 at a constant temperature. Points r and 1 are the inflections of the curve and point s is the passage through zero. The unit of measurement for thermoelectric power $\eta$ is $\mu V/K$.

Figure 1:
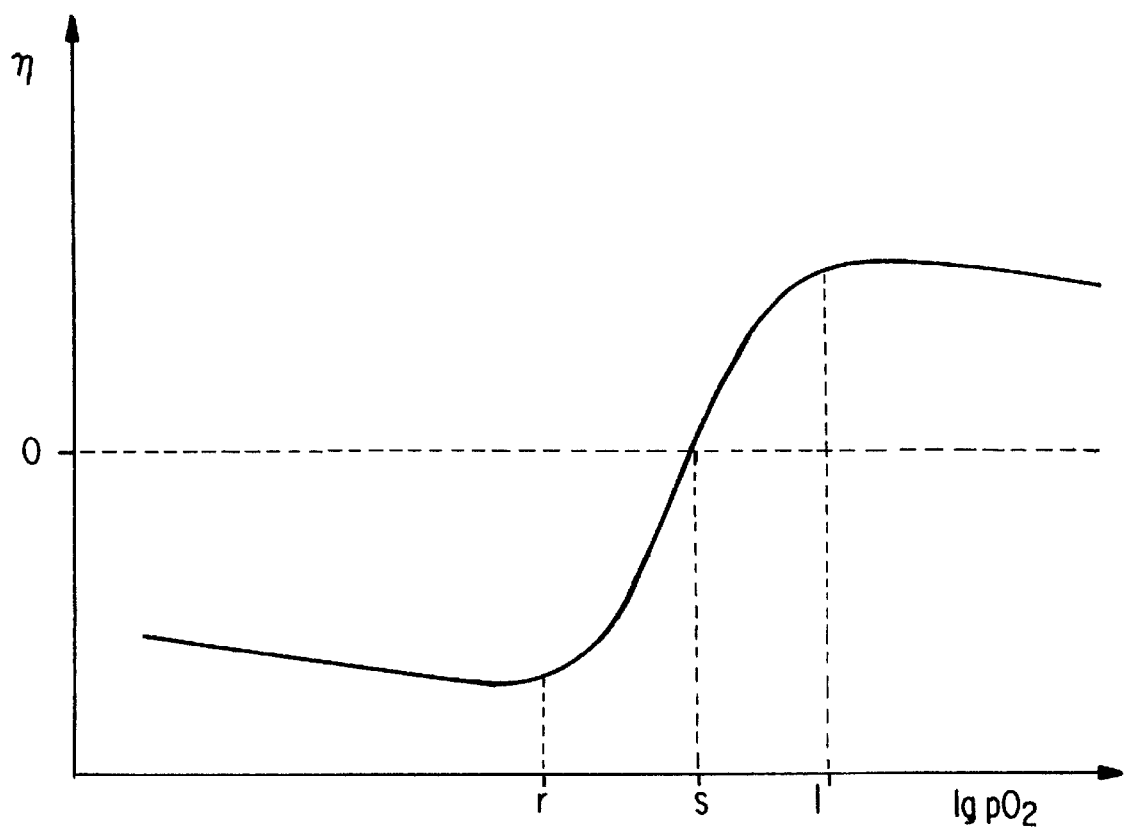
FIG. 1 is a logarithmic plot of a typical curve of thermoelectric power $\eta$ versus oxygen partial pressure $pO_2$ of a semiconducting metal oxide.

The curve in FIG. 1 (particularly points r, s, and 1) shifts with temperature. A detailed description of the well known thermoelectric power properties of metal oxide compounds can be found for example in Joffe A. F.: Physics of Semiconductors, Berlin 1958. In FIG. 1, there is electron conduction to the left of point s due to an oxygen deficit leading to negative thermoelectric power, and to the right of point s there is defect electron (hole) conduction due to excess oxygen.

Figure 2:
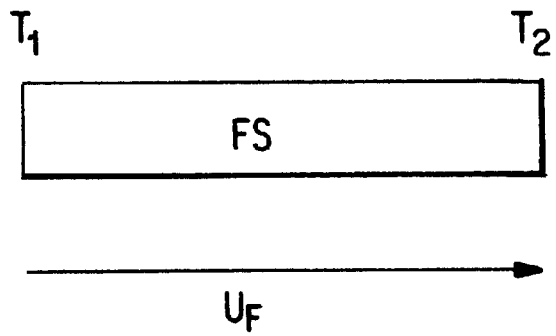
FIG. 2 is a schematic diagram of a measuring arrangement for measuring the thermoelectric power of a metal oxide.

The geometric data in the description below relate to FIG. 2. If a temperature $T_1$ prevails at one point on functional layer FS and a temperature $T_2$ at another point on functional layer FS, the thermoelectric voltage $U_F$.

$$U_F = \int_{T_1}^{T_2} \eta(T, pO_2) dT \quad (1)$$

can be measured between the two points. If there is only a small temperature difference $T_2-T_1$ $$U_F = \eta(T, pO_2) \times (T_2 - T_1) \quad (2)$$

applies approximately.

With a constant temperature difference $T_2-T_1$, $U_F$ is thus a measure of thermoelectric power $\eta(T, pO_2)$. Based on the known relationship between thermoelectric power and oxygen partial pressure, the oxygen partial pressure can be deduced. The temperature dependence of the thermoelectric power, which depends on the oxygen partial pressure, can be compensated by measuring temperature T.

If, in addition, the temperature difference $T_2-T_1$ is known, the thermoelectric power $\eta(T, pO_2)$ can be calculated from $U_F$ and the oxygen partial pressure calculated from the latter. Instead of measuring the temperature difference $T_2-T_1$ directly, it is of course also possible to measure the temperatures $T_2$ and $T_1$ individually, then calculate the thermoelectric power $\eta(T, pO_2)$ using $U_F$, and then calculate the oxygen partial pressure.

Figure 3:
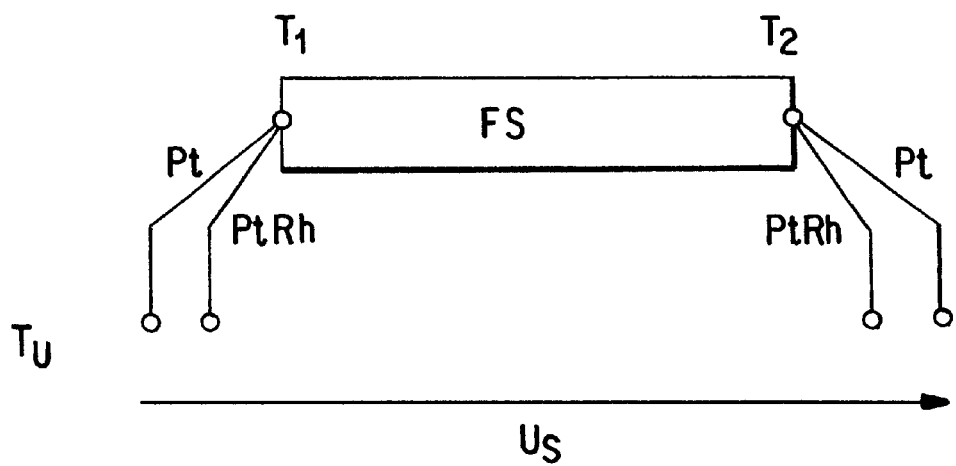
FIG. 3 is a schematic diagram of a measuring arrangement with two thermocouples for measuring the thermoelectric power of a metal oxide.
Figure 5:
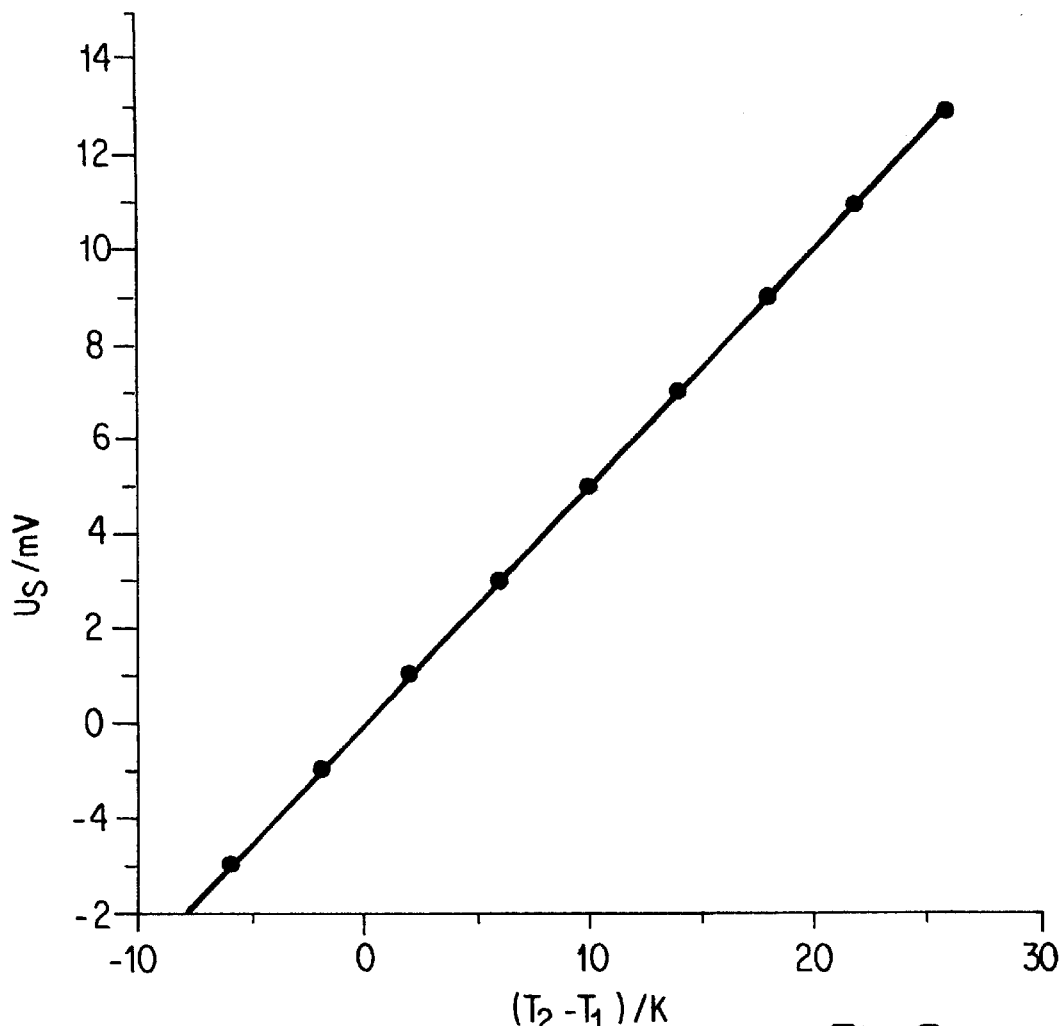
FIG. 5 is a graph of voltage as a function of temperature different.

A simple measurement can be made with the arrangement shown schematically in FIG. 3: On functional layer FS, a temperature difference $T_2-T_1$ is set and measured with the aid of the thermocouple pairs (for example, Pt—Pt 10% Rh). In addition, at the contact points that are at temperature $T_U$, voltage $U_S$ is measured, which in principle is composed of the sum of voltage $U_F$ and a thermal e.m.f. $U_T$, which results from the temperature difference between $T_1$ and $T_U$ or $T_2$ and $T_U$. Since the thermoelectric power of platinum is known, $U_T$ can be calculated. Another possible measuring method is to vary the temperature difference $T_2-T_1$ continuously, when the average of $T_2$ and $T_1$ will not change greatly, and hence to plot $T_2-T_1$ and $U_S$. In the graph $U_S(T_2-T_1)$ a curve results (shown in FIG. 5) whose gradient is the thermoelectric power $\eta$ to be determined. Any offset voltages present such as the thermal e.m.f. of platinum referred to above is reflected in the axis intercept of curve $U_S(T_2-T_1)$ and not in the gradient.

Figure 4:
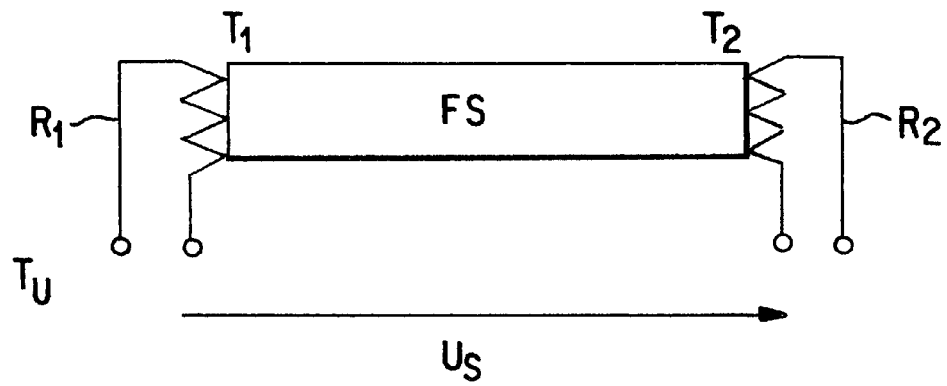
FIG. 4 is a schematic diagram of a measuring arrangement with two resistance thermometers to measure the thermoelectric power of a metal oxide.

Another simple measurement can be made with an arrangement shown schematically in FIG. 4: On functional layer FS, a temperature difference $T_2-T_1$ is set and measured with the aid of the two resistance thermometers R1, R2 (made of platinum for example). In addition, at the contact points that are at temperature $T_U$, voltage $U_S$ is measured, which in principle is composed of the sum of voltage $U_F$ and a thermal e.m.f. $U_T$, which results from the temperature difference between $T_1$ and $T_U$ or $T_2$ and $T_U$. Since the thermoelectric power of platinum is known, $U_T$ can be calculated. Another possible measuring method is to vary the temperature difference $T_2-T_1$ continuously, when the average of $T_2$ and $T_1$ will not change greatly, and hence to plot $T_2-T_1$ and $U_S$. In the graph $U_S(T_2-T_1)$ a curve results whose gradient is the thermoelectric power η to be determined. Any offset voltages present such as the thermal e.m.f. of platinum referred to above is in the axis intercept of curve $U_S(T_2-T_1)$ and not in the gradient.

Figure 6:
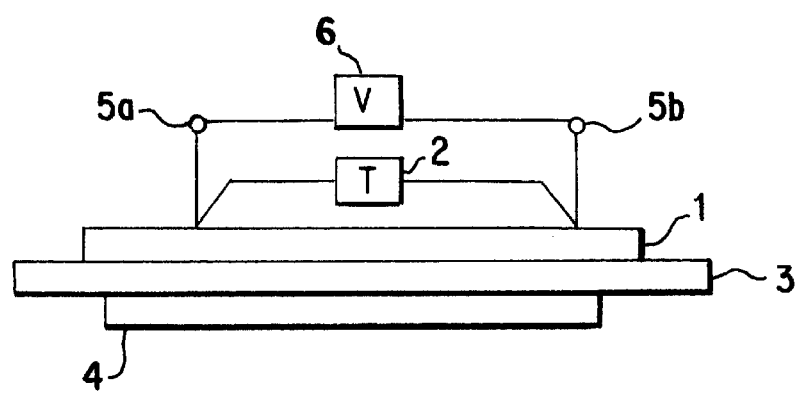
FIG. 6 is a schematic illustration of the layer structure of a transducer according to the invention.

A typical film technology structure, described below, is shown schematically in FIG. 6. A functional layer 1 provided with a temperature measuring device 2 according to FIG. 2 or FIG. 3 is placed on an electrically nonconducting substrate 3. A heating layer 4 is placed on the other flat side of the Substrate. Electrodes 5a, 5b for the voltage measurement are placed on the functional layer in thick film technology or thin film technology. A voltage detector 6 is connected to measure the voltage difference between the electrodes 5a and 5b.

Both the heating layer and the electrode and functional layer can be implemented in thick film technology and/or in thin film technology. It is also possible, however, to cast a film from the material of the function layer and apply this to a substrate provided with a temperature measuring device according to FIG. 2 or FIG. 3.

The functional layer can consist in particular of a doped multiple metal oxide, preferably based on titanate or ferrate.

It should be pointed out that the transducer according to the invention does not necessarily have to have a heater. The temperature difference can also be generated within the functional layer by other means. For example, when the sensor is placed in the exhaust line of an internal combustion engine, it is possible to bring the functional layer with the hot exhaust to the temperature.

It is also possible to use the temperature measuring resistors for heating purposes. Parts of the heater can also be wired as an electrode for the voltage measurements at the points on the functional layer that are at different temperatures.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Method for determining an oxygen concentration of a gas, comprising:
    providing a functional material in the form of a layer or film and made of a semiconducting metal oxide, whose thermoelectric power can be represented as a function of oxygen partial pressure;
    subjecting the functional material to the gas;
    generating a temperature difference between two points on the functional material;
    measuring a voltage difference between the two points of the functional material; and
    determining the oxygen concentration as a function of the measured voltage;
    wherein semiconducting metal oxide of the functional layer is a doped multiple metal oxide based on one of titanate and ferrate.

2. The method according to claim 1 wherein the temperature difference between the two points on the functional material is measured directly and incorporated into the determination of the oxygen concentration.

3. The method according to claim 2 wherein a temperature of at least one of the two points is measured additionally.

4. The method according to claim 1 wherein temperatures of the two points of the functional material are measured separately and incorporated into the determination of the oxygen concentration.

5. The method according to claim 3 wherein temperature dependence of thermoelectric power, which depends on oxygen partial pressure, is compensated by at least one of the temperatures determined.

6. The method according to claim 1, wherein temperature is measured by thermocouples and/or resistance thermometers.

7. The method according to claim 1, wherein the temperature difference between the points on the functional material is generated by a heater using layer or film heating.

8. The method according to claim 7 wherein parts of the heater are wired as an electrode for voltage measurements at the points on the functional layer that are at different temperatures.

9. The method according to claim 7 wherein parts of the heater are used for temperature measurement.

10. The method according to claim 1, wherein:
    the voltage difference between the two points of the functional material and any offset voltages the contacts of the voltage measuring instruments are measured; and
    measurement is made at several temperature differences, the measured values thus obtained being a measure of oxygen concentration.

11. A transducer for determining an oxygen content of a gas, comprising:
    an electrically nonconducting substrate having two flat sides;
    a functional material in the form of a layer or film and made of a semiconducting metal oxide, whose thermoelectric power can be represented as a function of oxygen partial pressure, and which is disposed on one flat side of the substrate;
    an electric heater in the form of a layer or film disposed on the other flat side of the substrate, with which a temperature difference can be generated between two points on the functional layer;
    two electrodes disposed at the two points on the functional layer provided for differing temperatures;
    means for determining temperature difference between the two points on the functional layer, for different temperatures; and
    means for determining a voltage difference between the two points on the functional material;
    wherein semiconducting metal oxide of the functional layer is a doped multiple metal oxide based on one of titanate and ferrate.

12. A transducer for determining an oxygen content of a gas according to claim 11 wherein said means for determining a temperature difference comprises means for determining respective temperatures at both of said two points.

13. The method for manufacturing a transducer for measuring an oxygen concentration of a gas, comprising:
    applying an electrical heater to one flat side of an electrically nonconducting substrate, using thick film technology or thin film technology;

applying a functional material on the other flat side of the substrate;

applying electrodes by thick film technology or thin film technology at the two preestablished points on the functional material which can be maintained at different temperatures; and providing one of thermocouples and resistance thermometers for determining a temperature difference, by thick film technology or thin film technology, at both the preestablished points on the functional material; wherein said functional material comprises, a layer or film made of a semiconducting metal oxide; and semiconducting metal oxide of the layer or film comprises a doped multiple metal oxide based on one of titanate and ferrate.

* * * * *